United States Patent [19]

Baltes et al.

[11] Patent Number: 4,525,358

[45] Date of Patent: Jun. 25, 1985

[54] 2-[4-(DIPHENYLMETHYL)-1-PIPERAZINYL]-ACETIC ACIDS AND THEIR AMIDES

[75] Inventors: Eugène Baltes, Rhode-St.Genese; Jean de Lannoy; Ludovic Rodriguez, both of Brussels, all of Belgium

[73] Assignee: UCB Pharmaceuticals, Inc., Dover, Del.

[21] Appl. No.: 496,489

[22] Filed: May 17, 1983

Related U.S. Application Data

[63] Continuation of Ser. No. 345,918, Feb. 4, 1982, abandoned.

[30] Foreign Application Priority Data

Feb. 6, 1981 [GB] United Kingdom ................. 8103768
Apr. 8, 1981 [GB] United Kingdom ................. 8110990

[51] Int. Cl.³ .................... A61K 31/50; C07D 295/14
[52] U.S. Cl. ..................................... 514/255; 544/396
[58] Field of Search ......................... 544/396; 424/250

[56] References Cited

U.S. PATENT DOCUMENTS

| 2,630,435 | 3/1953 | Baltzly et al. | 544/396 |
| 2,636,032 | 4/1953 | Weston et al. | 544/396 |
| 2,861,072 | 11/1958 | Weston | 544/396 |
| 2,899,436 | 8/1959 | Morren | 544/396 |
| 3,244,718 | 4/1966 | Biel | 260/268 |
| 3,267,104 | 8/1966 | Hermans et al. | 544/396 |

FOREIGN PATENT DOCUMENTS

| 222475 | 7/1957 | Australia | 544/396 |
| 763609 | 9/1971 | Belgium | 544/396 |

OTHER PUBLICATIONS

Burger, Alfred; *Medicinal Chemistry* 3rd, Wiley-Interscience, New York, pp. 55, 57, 58, 71 (1971)

Close et al., *Proc. Eur. Soc. Study Drug Toxicity*, 1968, 9, 144–155.
Pong et al., *J. Pharm. Sci.*, 1974, 63 (10), 1527–1532.
Fouda et al., *J. Pharm. Sci.*, 1979, 68 (11), 1456–1458.

*Primary Examiner*—Donald G. Daus
*Assistant Examiner*—G. Hendricks
*Attorney, Agent, or Firm*—Wenderoth, Lind & Ponack

[57] ABSTRACT

New 2-[4-(diphenylmethyl)-1-piperazinyl]-acetic acids, their amides and their salts, processes for the preparation thereof and therapeutic compositions. These compounds have the formula

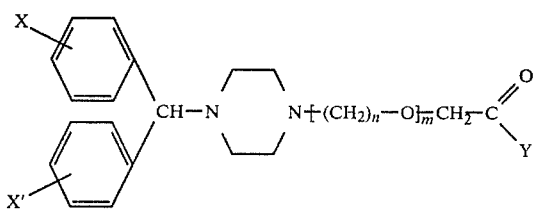

wherein Y=—OH or —NH$_2$; X and X'=H, halogen, alkoxy or trifluoromethyl; m=1 or 2 and n=1 or 2.

The amides of the 2-[4-(diphenylmethyl)-1-piperazinyl]-acetic acids are prepared either by reacting a 1-(diphenylmethyl)-piperazine with an omegahaloacetamide, or by reacting an alkali metal salt of an omega-[4-(diphenylmethyl)-1-piperazinyl]-alkanol with a 2-haloacetamide, or yet by reacting ammonia with a halide or alkyl ester of a 2-[4-(diphenylmethyl)-1-piperazinyl]-acetic acid, whereas the 2-[4-(diphenylmethyl)-1-piperazinyl]-acetic acids are prepared by hydrolyzing the corresponding amide or lower alkyl ester.

These compounds have in particular an antiallergic, spasmolytic and antihistaminic activity.

31 Claims, No Drawings

2-[4-(DIPHENYLMETHYL)-1-PIPERAZINYL]-ACETIC ACIDS AND THEIR AMIDES

This application is a continuation of application Ser. No. 345,918, filed Feb. 4, 1982 (now abandoned).

The present invention relates to new 2-[4-(diphenylmethyl)-1-piperazinyl]-acetic acids and the amides and non-toxic, pharmaceutically acceptable salts thereof, as well as to processes for the preparation thereof and to pharmaceutical compositions containing them.

The new compounds according to the present invention have the general formula:

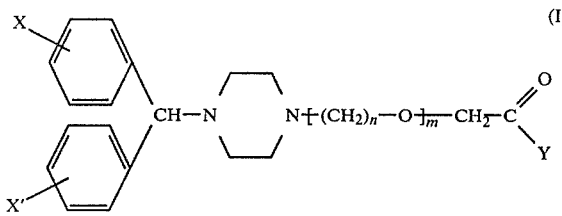

wherein
Y is a hydroxyl group or an $-NH_2$ group,
X and X' represents independently a hydrogen atom, a halogen atom, a straight or branched chain lower alkoxy radical or a trifluoromethyl radical,
m is 1 or 2, and
n is 1 or 2, preferably 2,
as well as the non-toxic, pharmaceutically acceptable salts thereof.

The term "lower alkoxy" as used herein means residues of both straight and branched chain aliphatic alcohols having from 1 to 4 carbon atoms, such as methoxy, ethoxy, propoxy and the like. The halogen atom is preferably a chlorine or fluorine atom.

The expression "non-toxic, pharmaceutically acceptable salts" are used herein means not only the addition salts of the acids and amides of formula I with pharmaceutically acceptable acids, such as acetic, citric, succinic, ascorbic, hydrochloric, hydrobromic, sulfuric and phosphoric acid, but also the pharmaceutically acceptable salts of the acids of formula I such as the metal salts (for example sodium or potassium salts), the ammonium salts, the amine salts and the aminoacid salts.

These pharmaceutically acceptable salts may be prepared from compounds of formula I by per se known methods.

The preferred compounds according to the present invention are:
2-[2-[4-[(4-chlorophenyl)phenylmethyl]-1-piperazinyl]ethoxy]-acetic acid and its dihydrochloride;
potassium 2-[2-[4-[(4-chlorophenyl)phenylmethyl]-1-piperazinyl]ethoxy]-acetate;
2-[2-[4-(diphenylmethyl)-1-piperazinyl]ethoxy]-acetic acid and its dihydrochloride;
2-[2-[4-[(4-fluorophenyl)phenylmethyl]-1-piperazinyl]ethoxy]-acetic acid and its hydrate.

The compounds of formula I possess interesting pharmacological properties. In particular, they are useful as antiallergic, antihistaminic, bronchodilatory and antispasmodic agents.

Furthermore, they are characterized by the fact that their secondary effects of stimulating or depressing the central nervous system, which are frequently observed in the case of conventional antihistaminic agents, are minimal. In addition, they display interesting anaesthetic and antiinflammatory properties and also display an activity in cases of cerebral and cardiovascular insufficiency.

In an article by H. B. WRIGHT and D. L. MARTIN (J. med. Chem. 11, (1968), 390-391) the activity of 2-[4-[(4-chlorophenyl)phenylmethyl]-1-piperazinyl]-acetamide (formula I: $Y=NH_2$; $X=p-Cl$; $X'=H$; but m=O) as a hypocholesteremic agent is studied but the results obtained were not very encouraging.

Furthermore, according to Belgian Patent Specification No. 763,609, 2-[4-(diphenylmethyl)-1-piperazinyl]-acetamide (formula I: $Y=NH_2$; $X=X'=H$; but m=O) possesses a diuretic activity. It also describes similar acetamides in which the nitrogen atom of the amide group is substituted and wich possess various other pharmacological properties.

The pharmacological tests which we have carried out demonstrate that the antiallergic, antispasmodic and antihistaminic activities of these acetamides, as well as of the corresponding acids, are of little interest (see B. Pharmacology).

A. PROCESSES OF PREPARATION

I. The amides of formula I ($Y=-NH_2$) may be prepared by several methods, namely:

I.1. reacting a 1-(diphenylmethyl)-piperazine of formula II with an omegahaloacetamide of formula III according to the following equation:

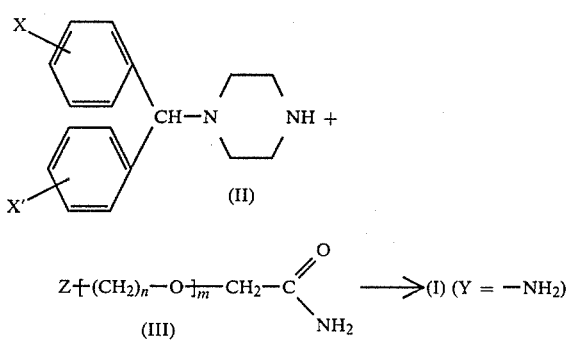

in which X, X', m and n have the same meanings as above and Z is a halogen atom.

This reaction is generally carried out by heating the reaction mixture to 80° to 150° C. for several hours in an inert solvent, which is preferably an aliphatic alcohol, an aliphatic ketone, for example methyl ethyl ketone, or an aromatic hydrocarbon, such as toluene or xylene, in the presence of an acid acceptor, such as a tertiary organic base, for example triethylamine, or an inorganic base, for example sodium carbonate.

I.2. reacting an alkali metal salt of an omega-[4-(diphenylmethyl)-1-piperazinyl]-alkanol of formula IV with a 2-haloacetamide of formula V according to the following equation:

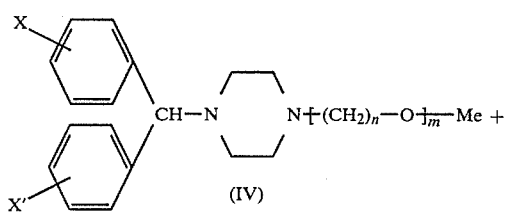

-continued

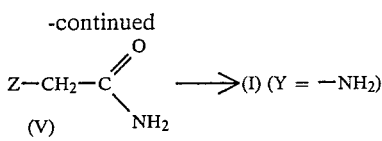
(V)

in which X, X', m and n have the same meanings as above, Z is a halogen atom and Me is an alkali metal atom.

The reaction between the alkali metal salt of formula IV and the haloacetamide of formula V is carried out in an inert solvent, for example toluene, xylene or dimethylformamide, at a temperature of from 0° C. to the reflux temperature of the reaction mixture.

The alkali metal salt of formula IV used in this reaction may be prepared in situ by reacting an appropriate omega-[4-(diphenylmethyl)-1-piperazinyl]-alkanol with an alkali metal hydride, generally with sodium hydride, in an inert solvent, such as toluene, xylene or dimethylformamide.

The preparation of the alcohols of formula IV (Me=H) is described in U.S. Pat. No. 2,899,436.

I.3. reacting ammonia with a functional derivative of a 2-[4-(diphenylmethyl)-1-piperazinyl]-acetic acid, namely a halide or a lower alkyl ester of formula VII, according to the following equation:

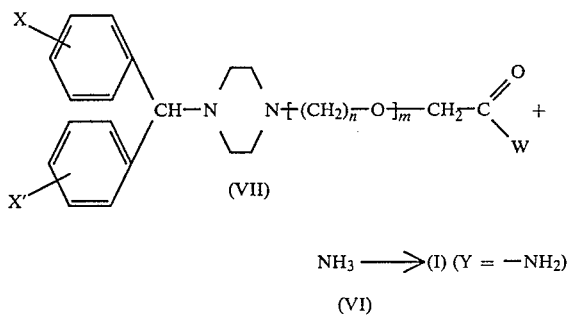

in which X, X', m and n have the same meanings as above and W represents a halogen atom or an —OR' radical, in which R' is a lower alkyl radical.

The halogen atom may be, for example, a chlorine or bromine atom and the alkyl radical may be, for example, a methyl or ethyl radical.

When W represents a halogen atom, an acid of formula I, in which Y is a hydroxyl group, is first prepared by method II described hereinafter, which is then converted into the corresponding halide by methods which are well known for the preparation of this type of compound. Subsequently, the acid halide thus obtained is reacted with ammonia in an inert solvent.

When W represents an —OR' radical, an ester of formula VII is first prepared by one of the methods described hereinafter. Subsequently, this ester is reacted with ammonia in an inert solvent, at a temperature of from 0° C. to ambient temperature. This reaction may possibly be carried out in the presence of a catalyst, such as sodium methoxide.

II. The acids of formula I, in which Y is a hydroxyl group, may be prepared by hydrolyzing, in a basic medium, a functional derivative of a 2-[4-(diphenylmethyl)-1-piperazinyl]-acetic acid, namely an amide or a lower alkyl ester of the formula:

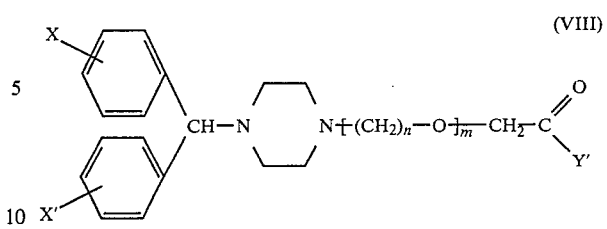

in which X, X', m and n have the same meanings as above and Y' represents an —NH₂ group or an —OR' group, in which R' is a lower alkyl radical, for example a methyl or ethyl radical.

This hydrolysis is carried out by means of an inorganic base, such as sodium or potassium hydroxide, in an aqueous or aqueous alcoholic medium, for example in aqueous methanol, ethanol or the like, at a temperature of from 20° C. to the reflux temperature of the reaction mixture.

The amides of formula VIII, in which Y' is —NH₂, may be prepared by one of methods I.1 to I.3 described above.

With regard to the esters of formula VII, in which W is —OR', and the esters of formula VIII, in which Y' is —OR', these may be prepared by various methods, for example:

(a) reacting a 1-(diphenylmethyl)-piperazine of the formula II with a lower alkyl omega-haloacetate of the formula IX, according to the following equation:

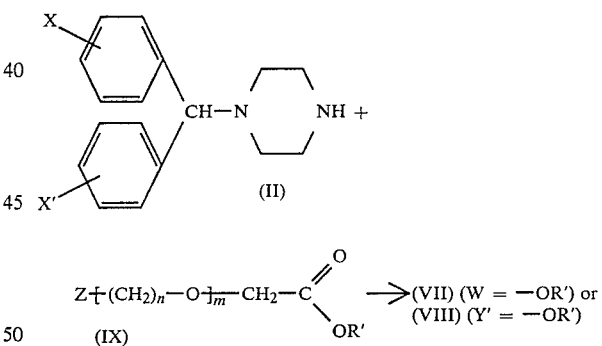

in which X, X', m and n have the same meanings as above, R' is a lower alkyl radical and Z is a halogen atom. Thus, R' may be, for example, a methyl or ethyl radical and Z may be a chlorine or bromine atom.

This reaction is generally carried out by heating the reaction mixture to a temperature of from 80° to 150° C. for several hours in an inert solvent, such as benzene, toluene or xylene, in the presence of an acid acceptor, such as a tertiary organic base, for example triethylamine, or an inorganic base, for example sodium carbonate;

(b) reacting an alkali metal salt of an omega-[4-(diphenylmethyl)-1-piperazinyl]-alkanol of formula IV with a lower alkyl ester of a 2-haloacetic acid of formula X according to the following equation:

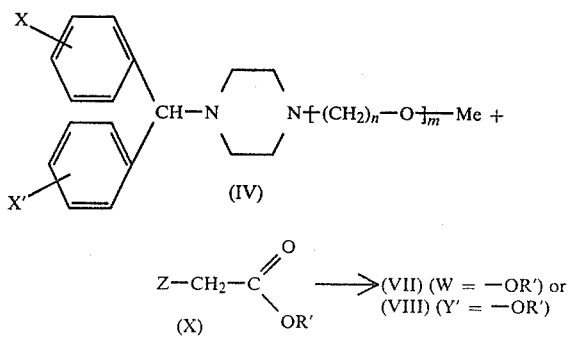

in which R', X, X', m and n have the same meanings as above Z is a halogenatom and Me is an alkali metal atom.

The reaction between the alkali metal salt of formula IV and the halogenated ester of formula X is carried out in an inert solvent at a temperature of from 0° C. to the reflux temperature of the reaction mixture.

The following Examples are given for the purpose of illustrating the present invention:

EXAMPLE 1

Preparation of amides of formula I (Y=—NH$_2$)

1.1.

2-[2-[4-Diphenylmethyl)-1-piperazinyl]ethoxy]-acetamide dihydrochloride (method I.1)

A mixture of 37.8 g (0.15 mole) of 1-(diphenylmethyl)-piperazine, 27.5 g (0.2 mole) of 2-(2-chloroethoxy)-acetamide and 26.5 g of anhydrous sodium carbonate in 120 ml of xylene is heated for 4 hours to 90° to 120° C. Thereafter, 120 ml of benzene are added to the reaction mixture, the precipitate formed is filtered off and the organic phase is extracted with dilute hydrochloric acid (30 ml of concentrated hydrochloric acid and 100 ml of water). 40 ml of a concentrated aqueous solution of sodium hydroxide are added, followed by extraction with benzene. The benzene solution is washed with water, dried over anhydrous sodium carbonate and the benzene is evaporated off to dryness. The evaporation residue is triturated with diethyl ether and left to crystallize. 2-[2-[4-(Diphenylmethyl)-1-piperazinyl]ethoxy]-acetamide is obtained in a yield of 73% of theory; M.P. 119°–120° C.

The dihydrochloride, prepared in ethanol, melts at 230° C., with decomposition.

| Analysis for C$_{21}$H$_{27}$N$_3$O$_2$.2 HCl in % | | | | |
|---|---|---|---|---|
| calc.: | C 59.15 | H 6.85 | N 9.85 | Cl$^-$ 16.63 |
| found: | 58.99 | 6.80 | 9.79 | 16.46 |

The following compounds are also prepared by the above-described method:

2-[2-[4-[(4-chlorophenyl)phenylmethyl]-1-piperazinyl]ethoxy]-acetamide; yield 47% of theory; M.P. 111°–112° C., after recrystallization from ethanol.

| Analysis for C$_{21}$H$_{26}$ClN$_3$O$_2$ in % | | | | |
|---|---|---|---|---|
| calc.: | C 65.02 | H 6.71 | N 10.83 | Cl 9.14 |
| found: | 64.59 | 7.00 | 10.82 | 9.54 |

2-[2-[2-[(4-diphenylmethyl)-1-piperazinyl]ethoxy]ethoxy]-acetamide; the product, obtained in a crude state in a practically quantitative yield, may be used as such, without further purification, for the preparation of the corresponding acid (see Example 2.2).

2-[2-[2-[4-[(4-chlorophenyl)phenylmethyl]-1-piperazinyl]ethoxy]ethoxy]-acetamide; the product, obtained in a crude state in a practically quantitative yield, may be used as such, without further purification, for the preparation of the corresponding acid (Example 2.2).

2-[2-[4-[(4-fluorophenyl)phenylmethyl]-1-piperazinyl]ethoxy]-acetamide; yield 54.7% of theory; M.P. 105°–107° C., after recrystallization from acetonitrile.

| Analysis for C$_{21}$H$_{26}$FN$_3$O$_2$ in % | | | |
|---|---|---|---|
| calc.: | C 67.90 | H 7.09 | N 11.31 |
| found: | 63.3 | 7.40 | 11.21 |

2-[2-[4-[(2-chlorophenyl)phenylmethyl]-1-piperazinyl]ethoxy]-acetamide; yield 57% of theory; M.P. 129°–130° C., after recrystallization from benzene.

| Analysis for C$_{21}$H$_{26}$ClN$_3$O$_2$ in % | | | | |
|---|---|---|---|---|
| calc.: | C 65.0 | H 6.75 | N 10.8 | Cl 9.4 |
| found: | 66.3 | 7.0 | 10.6 | 9.7 |

The dihydrochloride of this amide has also been prepared; it contains some monohydrochloride. M.P. 218°–220° C., after recrystallization from isopropyl alcohol.

| Analysis for C$_{21}$H$_{26}$ClN$_3$O$_2$.2 HCl in % | | | | | |
|---|---|---|---|---|---|
| calc.: | C 54.72 | H 6.12 | N 9.11 | Cl$^-$ 15.38 | Cl$^{total}$ 23.08 |
| found: | 55.69 | 6.52 | 9.20 | 11.86 | 20.27 |

2-[2-[4-[(4-methoxyphenyl)phenylmethyl]-1-piperazinyl]ethoxy]-acetamide dihydrochloride; yield 20% of theory; M.P. 175°–176° C. after recrystallization from acetonitrile.

| Analysis for C$_{22}$H$_{29}$N$_3$O$_3$.2 HCl in % | | | | |
|---|---|---|---|---|
| calc.: | C 57.8 | H 6.8 | N 9.2 | Cl$^-$ 15.5 |
| found: | 57.8 | 7.2 | 9.5 | 15.9 |

2-[2-[2-[4-[[4-(trifluoromethyl)phenyl]phenylmethyl]-1-piperazinyl]ethoxy]ethoxy]-acetamide;

2-[2-[2-[4-[bis(4-fluorophenyl)methyl]-1-piperazinyl]-ethoxy]ethoxy]-acetamide.

1.2.

2-[2-[2-[4-(Diphenylmethyl)-1-piperazinyl]ethoxy]ethoxy]-acetamide dihydrochloride. (method I.2).

24.2 g (0.53 mole) of sodium hydride are added to a solution of 172.9 g (0.508 mole) of 2-[2-[4-(diphenylmethyl)-1-piperazinyl]ethoxy]-ethanol in 180 ml of dimethylformamide. When the addition is finished, the reaction mixture is heated to 40° C. for 30 minutes. After cooling, 60 g (0.624 mole) of 2-chloroacetamide are added thereto in the course of 10 minutes. The temperature of the reaction mixture increases to 40° C. and is maintained at this temperature for a further 30 minutes. After cooling, 30 ml of water are added, followed by evaporation to dryness. The evaporation residue is suspended in 1 liter water and the suspension obtained is extracted with benzene. The organic phase is dried over anhydrous potassium carbonate and then evaporated. The evaporation residue is purified by chromatography on a column of silica (eluent: chloroform-ethanol 95:5 v/v). The product obtained is dissolved in 45 ml of ethanol, to which are added 24 ml of a 5.1 N ethanolic solution of hydrochloric acid. There are obtained 19 g of 2-[2-2-[4-(diphenylmethyl)-1-piperazinyl]ethoxy]ethoxy]-acetamide dihydrochloride in a yield of 8% of theory; M.P. 196°–197° C., after recrystallization from acetonitrile.

| Analysis for $C_{23}H_{31}N_3O_3 \cdot 2$ HCl in % | | | | |
|---|---|---|---|---|
| calc.: | C 58.72 | H 7.07 | N 8.93 | $Cl^-$ 15.07 |
| found: | 58.29 | 6.83 | 8.44 | 15.01 |

The following compound is prepared by the above-described method:
2-[2-[2-[4-[(4-chlorophenyl)phenylmethyl]ethoxy]ethoxy]-acetamide dihydrochloride; the product recrystallizes from isopropyl alcohol with one molecule of solvent of crystallization. Yield 11% of theory; M.P. 100°–102° C.

| Analysis for $C_{23}H_{30}ClN_3O_3 \cdot C_3H_7OH \cdot 2$ HCl in % | | | | |
|---|---|---|---|---|
| calc.: | C 55.27 H 7.16 | N 7.43 | $Cl^-$ 12.55 | $Cl^{total}$ 18.22 |
| found: | 53.10 6.93 | 7.18 | 12.56 | 18.79 |

1.3.
2-[2-[4[(4-Chlorophenyl)phenylmethyl]-1-piperazinyl]ethoxy]-acetamide. (method I.3)

2.3 g (0.0057 mole) of methyl 2-[2-[4-[(4-chlorophenyl)phenylmethyl]-1-piperazinyl]ethoxy]-acetate are dissolved in 100 ml of anhydrous methanol. This solution is cooled to a temperature of 5° to 10° C. and then ammonia is bubbled through for 20 hours. The solvent is evaporated off in a vacuum and the residue is triturated with diethyl ether and left to crystallize, 1.2 g of 2-[2-[4-[(4-chlorophenyl)phenymethyl]-1-piperazinyl]ethoxy]-acetamide being obtained; yield 54% of theory; M.P. 109°–110° C.

| Analysis for $C_{21}H_{26}ClN_3O_2$ in % | | | | |
|---|---|---|---|---|
| calc.: | C 65.02 | H 6.71 | N 10.83 | Cl 9.14 |
| found: | 65.13 | 6.59 | 10.95 | 9.54 |

The methyl 2-[2-[4-[(4-chlorophenyl)phenylmethyl]-1-piperazinyl]ethoxy]-acetate used as starting material is prepared in the following manner:

A mixture 87 g (0.30 mole) of 1-[(4-chlorophenylmethyl]-piperazine, 58 g (0.38 mole) of methyl (2-chloroethoxy)-acetate and 40.3 g (0.38mole) of sodium carbonate in 500 ml anydrous xylene is heated under reflux for 40 hours, with good stirring. The reaction mixture is then cooled and filtered and the solid is washed with benzene, the washed solid being discarded. The filtrate is evaporated to dryness and the evaporation residue is purified by chromatography on a column of silica (eluent: chloroform:methanol 97:3 v/v), 34 g (27.8% of theory) of the desired method ester thus being obtained.

| Analysis for $C_{22}H_{27}ClN_2O_3$ in % | | | |
|---|---|---|---|
| calc.: | C 65.60 | H 6.70 | N 6.95 |
| found: | 63.87 | 6.55 | 6.59 |

The following two addition salts of this ester were also prepared:
the dihydrochloride; M.P. 123°–125° C.

| Analysis for $C_{22}H_{27}ClN_2O_3 \cdot 2$ HCl in % | | | | |
|---|---|---|---|---|
| calc.: | C 55.50 | H 6.10 | N 5.89 | $Cl^-$ 14.92 |
| found: | 55.20 | 6.23 | 5.65 | 13.2 | the dimaleate; M.P. 128°–130° C.

| Analysis for $C_{30}H_{35}ClN_2O_{11}$ in % | | | |
|---|---|---|---|
| calc.: | C 56.70 | H 5.51 | N 4.41 |
| found: | 57.01 | 5.22 | 4.45 |

EXAMPLE 2
Preparation of acids of formula I (Y=OH).

2.1
2[2-[4-[(4-Chlorophenyl)phenylmethyl]-1-piperazinyl]ethoxy]-acetic acid. (method II).

16.8 g (0.0417 mole) of methyl 2-[2-[4-[(4-chlorophenyl)phenylmethyl]-1-piperazinyl]ethoxy]-acetate (prepared in the manner described above in Example 1.3) are dissolved in 65 ml of absolute ethanol. 42 ml of a 1 N ethanolic solution of potassium hydroxide are then added thereto and the reaction mixture is heated under reflux for 4 hours. It is then cooled and the precipitate removed by filitration, after washing with diethyl ether. The filtrate is evaporated to dryness and the evaporation residue is triturated with diethyl ether aand left to crystallize, 10.5 g of hydroscopic potassium 2-[2-[4-[(4-chlorophenyl)phenylmethyl]-1-piperazinyl]ethoxy]-acetate being obtained. The yield is 56% of theory; M.P. 161°–163° C.

| Analysis for $C_{21}H_{24}ClN_2O_3K$ in % | | | |
|---|---|---|---|
| calc.: | C 59.0 | H 5.63 | N 6.56 |
| found: | 57.97 | 5.77 | 6.48 |

The potassium salt is dissolved in 100 ml of water and adjusted with 10% hydrochloric acid to a pH of 4. The solution is extracted with chloroform and the organic phase is dried over anhydrous magnesium sulfate, whereafter it is evaporated to dryness. The evaporation residue is triturated with diethyl ether and left to crystallize, 7.5 g of 2-[2-[4-[(4-chlorophney)phenylmethyl[-1-piperazinyl]ethoxy]-acetic acid being obtained. Yield 81% of theory; M.P. 110°–115° C.

| Analysis for $C_{21}H_{25}ClN_2O_3$ in % | | | |
|---|---|---|---|
| calc.: | C 64.80 | H 6.48 | N 7.20 |
| found: | 62.3 | 6.48 | 6.92 |

The corresponding dihydrochloride, prepared in toluene in a yield of 80% of theory, melts at 225° C.

Analysis for C₂₁H₂₅ClN₂O₃.2 HCl in %

| | | | | |
|---|---|---|---|---|
| calc.: C 54.60 | H 5.85 | N 6.07 | Cl⁻ 15.38 | Cl$^{total}$ 23.07 |
| found: 54.42 | 5.60 | 6.01 | 15.29 | 23.08 |

2.2
2-[2-[4-(Diphenylmethyl)-1-piperazinyl]ethoxy]-acetic acid. (method II).

A mixture of 19 g (0.054 mole) of 2-[2-[4-(diphenyl-methyl)-1-piperazinyl[ethoxy[-acetamide (prepared in the manner described in Example 1.1) in 200 ml of ethanol and 27 ml of a 4 N ethanolic solution of sodium hydroxide is heated under reflux for 3 hours. The reaction mixture is adjusted with 29.7 ml of 3.61 N hydrochloric acid to a pH of 6.3, whereafter the ethanol is evaporated off in a vacuum. The precipitate obtained is filtered off. After evaporation of the solvent, 17.4 g of crude 2-[2-[4-(diphenylmethyl)-1-piperazinyl]ethoxy]-acetic acid are obtained. Yield 91% of theory; M.P. 100° C.

Analysis for C₂₁H₂₆N₂O₃ in %

| | | | |
|---|---|---|---|
| calc.: | C 71.1 | H 7.39 | N 7.90 |
| found: | 69.1 | 7.07 | 7.12 |

The corresponding dihydrochloride melts are 217°–218° C., after recrystallization from isopropyl alcohol.

Analysis for C₂₁H₂₆N₂O₃.2 HCl in %

| | | | | |
|---|---|---|---|---|
| calc.: | C 59.02 | H 6.60 | N 6.55 | Cl⁻ 16.59 |
| found: | 58.83 | 6.94 | 6.33 | 15.90 |

The following compounds are prepared by the above-described method:

2-[2-[2-[4-(diphenylmethyl)-1-piperazinyl]ethoxy]e-thoxy]-acetic acid dihydrochloride; yield 57% of theory; M.P. 85° C. (lyophylized; decomposition).

Analysis for C₂₃H₃₀N₂O₄.2 HCl in %

| | | | | |
|---|---|---|---|---|
| calc.: | C 58.60 | H 6.84 | N 5.94 | Cl⁻ 15.04 |
| found: | 56.82 | 7.82 | 6.02 | 16.76 |

2-[2-[2-[4-[(4-chlorophenyl)phenylmethyl]-1-piperazinyl]ethoxy]ethoxy]-acetic acid dihydrochloride; yield 82% of theory; M.P. 112° C. (lyophylized).

Analysis for C₂₃H₂₉ClN₂O₄.2 HCl in %

| | | | | |
|---|---|---|---|---|
| calc.: | C 54.6 | H 5.78 | N 5.54 | Cl$^{total}$ 21.03 |
| found: | 52.48 | 6.10 | 5.72 | 22.19 |

2-[2-[4-[(4-fluorophenyl)phenylmethyl]-1-piperazinyl]ethoxy]-acetic acid hydrate; yield 100% of theory; M.P. not sharp (from 70° C. onwards the product softens gradually).

Analysis for C₂₁H₂₅FN₂O₃.3/2 H₂O in %

| | | | |
|---|---|---|---|
| calc.: | C 63.1 | H 7.0 | N 7.0 |
| found: | 63.7 | 7.6 | 6.9 |

2[2-[4-[(4-methoxyphenyl)phenylmethyl]-1-piperazinyl]ethoxy]-acetic acid dihydrochloride; yield 35% of theory; M.P. 214°–217° C. (acetonitrile; decomposition).

Analysis for C₂₂H₂₈N₂O₄.2 HCl in %

| | | | | |
|---|---|---|---|---|
| calc.: | C 57.7 | H 6.6 | N 6.1 | Cl⁻ 15.5 |
| found: | 53.2 | 6.5 | 6.0 | 17.5 |

2-[2-[4-[(2-chlorophenyl)phenylmethyl]-1-piperazinyl]ethoxy]-acetic acid; yield 50% of theory; M.P. 96°–100° C. (lyophylized).

Analysis for C₂₁H₂₅ClN₂O₃ in %

| | | | | |
|---|---|---|---|---|
| calc.: | C 64.8 | H 6.5 | N 7.2 | Cl 9.1 |
| found: | 62.3 | 6.9 | 6.9 | 10.2 |

2-[2-[2-[4-[[4-(trifluoromethyl)phenyl]phenylmethyl]-1-piperazinyl]ethoxy]ethoxy]-acetic acid.
2-[2-[2-[4-[bis(4-fluorophenyl)methyl]-1-piperazinyl]ethoxy]ethoxy]-acetic acid.

B. PHARMACOLOGY

The following compounds according to the present invention were subjected to pharmacological testing and gave the results described hereinafter:

2-8 2-[4-(diphenylmethyl)-1-piperazinyl]ethoxy]-acetamide dihydrochloride (compound A, prepared in Example 1.1);

2-[2-[4-[(4-chorophenyl)phenylmethyl]-1-piperazinyl]ethoxy]-acetamide (compound B, prepared in Examples 1.1 and 1.3);

2-[2-[4-[(4-fluorophenyl)phenylmethyl]-1-piperazinyl]ethoxy]-acetamide (compound C, prepared in Example 1.1);

2-[2-[4-[(2-chlorophenyl)phenylmethyl]-1-piperazinyl]ethoxy]-acetamide dihydrochloride (compound D, prepared in Example 1.1);

2-[2-[4-[(4-methoxyphenyl)phenylmethly]-1-piperazinyl]ethoxy]-acetamide dihydrochloride (compound E, prepared in Example 1.1);

2[2-[2-[4-(diphenylmethyl)-1-piperazinyl]ethoxy]ethoxy]-acetamide dihydrochloride (compound F, prepared in Example 1.2);

2-[2-[2-[4-[(4-chlorophenyl)phenylmethyl]-1-piperazinyl]ethoxy]ethoxy]-acetamide dihydrochloride (compound G, prepared in Example 1.2);

potassium 2-[2-[4-[(4-chlorophenyl)phenylmethyl]-1-piperazinyl]ethoxy]-acetate (compound H, prepared in Example 2.1);

2-[2-[4-[(4-chlorophenyl)phenylmethyl]-1-piperazinyl]ethoxy]-acetic acid (compound I, prepared in Example 2.1);

2-[2-[4-[(4-chlorophenyl)phenylmethy]-1-piperazinyl]ethoxy]-acetic acid dihydrochloride (compound J, prepared in Example 2.1);

2-[2-[4-(diphenylmethyl)-1-piperazinyl]ethoxy]-acetic acid (compound K, prepared in Example 2.2);

2-[2-[2-[4-(diphenylmethyl)-1-piperazinyl]ethoxy]ethoxy]-acetic acid dihydrochloride (compound L, prepared in Example 2.2);

2-[2-[2-[4-[(4-chlorophenyl)phenylmethyl]-1-piperazinyl]ethoxy]ethoxy]-acetic acid dihydrochloride (compound M, prepared in Example 2.2);

2-[2-[4-[(4-fluorophenyl)phenylmethyl]-1-piperazinyl]e-
thoxy]-acetic acid hydrate (compound N, prepared in
Example 2.2);

The following compounds, which are not according
to the present invention (general formula I but in which
m=0) were also submitted to the same pharmacological
testing:

2-[4-(diphenylmethyl)-1-piperazinyl]-acetamide (compound 1, prepared by the method described in Belgian Patent Specification No. 763,609); M.P. 204° C.

2-[4-(4-chlorophenyl)phenylmethyl]1-piperazinyl]-
acetamide (compound 2; see H. B. WRIGHT and D. L. MARTIN, loc.cit; also prepared by the method described in Belgian Patent Specification No. 763,609); M.P. 145° C.

2-[4-(diphenylmelthyl)-1-piperazinyl]-acetic acid( compound 3, prepared by method II, Example 2.2); M.P. 176° C.

2-[4-[4-chlorophenyl)phenylmethyl]-1-piperazinyl]-
acetic acid (compound 4, also prepared by method II, Example 2.2); M.P. 106°-108° C.

1. Antiallergic activity.

This activity is determined in rats by means of the passive cutaneous anaphylaxis test (PCA) (see J. GOOSE and A. M. J. N. BlAIR, Immunology, 16, (1969), 749-760; and U. MARTIN and D. ROEMER, Arzneimittel-Forschung, 28, (5), (1978), 770-782).

Female rats are used, the sides of which have been partly shaved. Into the zone thus shaved there is injected intradermally, for passive sensitization of the animals, 0.05 ml of IGE antiovalbumin serum at a dilution such that, at the time of the PCA test, a distinct spot with a surface area of about 100 mm² appears at the point of injection.

72 Hours after the injection, 0.25 ml of a solution of allergen containing a coloring agent (5 mg of ovalbumin and 6 mg of Evans Blue in 0.25 ml of a 0.9% aqueous solution of sodium chloride) is administered intravenously. At the point of intradermal injection, there appears a distinct blue spot, the surface of which is measured.

In order to test the activity of the compounds according to the present invention, the procedure is carried out in the same manner; however, the test compound is administered orally 72 hours after injection of the serum;

15 minutes after this administration, 0.25 ml of the solution of the allergen is injected intravenously;

30 minutes after the administration of the allergen, the surface of the blue spot is measured.

The following Table I gives the immunological doses (ID 50 in μmol/kg) which bring about, on average of the total number of animals submitted to the test, a reduction of 50% of the surface area of the colored spot.

From this table, it can be seen that the compounds of the present invention are active when administered per os, while sodium cromoglycate is inactive in this mode of administration, even though it is well known for its antiasthmatic activity when administered intravenously. On the other hand, compounds 1, 2, 3 and 4 (not according to the present invention; m=0) prove to be of little interest.

TABLE I

| test compound | ID 50 per os in μmol/kg |
|---|---|
| sodium cromoglycate | inactive |

TABLE I-continued

| test compound | ID 50 per os in μmol/kg |
|---|---|
| B | 36.5 |
| C | 18.9 |
| F | 10.6 |
| N | 10.2 |
| 1 | >320 |
| 2 | >320 |
| 3 | >320 |
| 4 | >320 |

2. Spasmolytic and antihistaminic activity.

These activities are measured in the guinea pig by the method of H. KONZETT and R. ROESSLER (Naunyn-Schmiedebergs Arch. exp. Path. Pharmakol. 195, (1940), 71-74) an compared with those of theophylline.

Anaesthetized and curarized guinea pigs are subjected to artificial ventilation. The endotracheal pressure is recorded. Repetitive bronchial spasms are induced by successive and progressive intravenous injections of serotonin and histamine, respectively. The test compounds are also administered intravenously. The following Table II shows the doses of the compounds (ID 50 μmol/kg) which inhibit 50%, on average of the total number of animals, of the induced bronchospasms:

TABLE II

| Test compound | Serotonin | Histamine |
|---|---|---|
| Theophylline | 10 | 10 |
| A | 0.78 | 0.23 |
| B | 0.88 | 0.45 |
| C | 0.94 | 0.71 |
| D | 1.1 | 0.63 |
| E | 10.0 | 0.67 |
| F | 0.32 | 0.25 |
| G | 0.66 | 1.14 |
| H | 7.0 | 0.23 |
| I | 9.44 | 0.205 |
| J | 7.3 | 0.20 |
| K | 9.5 | 0.093 |
| L | 5.69 | 0.39 |
| M | 10.0 | 0.79 |
| N | 2.1 | 0.08 |
| 1 | 77 | 2.1 |
| 2 | 11 | 3.1 |
| 3 | >32 | 5 |
| 4 | >32 | 7.8 |

The compounds of the present invention are devoid of cholinergic activity. It can be seen from this Table that the compounds of the present invention possess a remarkably good activity with regard to bronchospasms induced by serotonin and histamine, respectively, with a more marked selectivity towards the latter. In contradistinction thereto, compounds 1, 2, 3 and 4 (not according to the invention; m=0) prove to be considerbly less active.

Furthermore, this test has shown the some of the compounds administered at a single dose possess an antihistamic activity of long duration. Thus, for example, compound J, administered in travenously to the guinea pig at a dose 1 of μmol/kg, still retains an activity of 100% after 5 hours.

3. General behaviour of mice (Irwin's test).

The behaviour is studied by means of Irwin's test (see S. IRWIN, "General philosophy and methodology of screening: a multidimensional approach"; Gordon Research Conference on Medicinal Chemistry, Aug. 3–7, 1959, at Colby Junior College, New London).

Progressive doses of the test compounds are administered intraperitoneally to groups of three male mice (body weight 18 to 22 g) and the general behaviour of the animals is observed according to known criteria.

The following reference compounds are used:
hydroxyzine=2-[2-[4-[(4-chlorophenyl)phenylmethyl]-1-piperazinyl]-ethoxy]-ethanol.
oxazepm=7-chloro-1,3-dihydro-3-hydroxy-5-phenyl:2H-1,4-benzodiazepin-2-one.

The following Table III gives the doses (in mg/kg) which induce the first manifestations of tranquilization in the animals:

TABLE III

| Test Compound | Tranquilizing dose in mg/kg |
|---|---|
| A | >255 |
| B | 38.7 |
| C | 115 |
| D | >460 |
| E | 136 |
| F | 94 |
| G | 34 |
| H | 46.2 |
| J | 138 |
| K | 106 |
| L | 141 |
| M | 505 |
| N | 372 |
| Hydroxyzine | 27 |
| Oxazepam | 2.6 |

It can be seen from this Table that the compounds according to the invention have little sedative effect in comparison with the reference compounds.

Furthermore, in this test, the toxicity of the compounds according to the present invention proves to be very low.

In the following Table IV, the lethal doses in mg/kg (two animals out of three) are given for compounds of the invention when administered intraperitoneally in mice:

TABLE IV

| Test compound | Lethal dose ($\frac{2}{3}$) in mg/kg |
|---|---|
| A | 255 |
| B | 232 |
| C | 386 |
| D | 460 |
| E | 456 |
| F | 282 |
| G | 339 |
| H | 277 |
| I | 116 |
| J | 138 |
| K | 708 |
| L | 942 |
| M | 505 |
| N | 372 |

If Tables III and IV (tranquilizing dose and lethal dose) are compared, it can be seen that for certain compounds the sedative effect only appears at a dose which is near the lethal dose.

4. DL 50 Lethal dose.

The low toxicity of the compounds according to the present invention has been confirmed by the measure of the DL 50 toxicity when administered per os. Thus, for compound J, in Wistar rats DL 50 is 703 mg/kg for the male rat and 865 mg/kg for the female rat.

In mice, the DL 50 for the same compound is respectively 600 mg/kg (male mouse) and 752 mg/kg (female mouse).

POSOLOGY AND ADMINISTRATION.

The pharmaceutical compositions containing the compounds of the present invention may be administered orally, parenterally or rectally. They may also be administered by nasal instillation (aerosols) or in the form of unguents or creams. The pharmaceutical compositions which can be used for oral administration may be solid or liquid, for example, in the form of uncoated or coated tablets, pills, dragees, gelatine capsules, solutions, syrups and the like. The compositions which can be used for parenteral administration may be any of those pharmaceutical compositions known for this mode of administration, for example, aqueous or oily solutions, suspensions or emulsions. For administration by the rectal route, the compositions containing the compounds of the present invention are generally used in the form of suppositories.

The pharmaceutical forms, such as injectable solutions, injectable suspensions, tablets, drops, suppositories and the like, are prepared by conventional pharmaceutical methods. The compounds of the present invention are mixed with a solid or liquid, non-toxic and pharmaceutically acceptable carrier and possibly also mixed with a dispersing agent, a distintegration agent, a stablilizing agent and the like. If appropriate, it is also possible to add preservations, sweeteners, coloring agents and the like.

The percentage of active compound in the pharmaceutical compositions may be varied within wide limits, according to the patient and the mode of administration and, in particular, the frequency of administration.

With regard to the posology, it may be varied within a wide range of dosage units, for example from 0.5 to 250 mg of active compound.

As an Example of a composition containing a compound of the present invention, the following formulation of a gelatine capsule for administration per os is given:

| compound J | 100 mg |
|---|---|
| lactose | 67 mg |
| magnesium stearate | 1 mg |
| silicon dioxide (Aerosil) | 2 mg |

We claim:
1. A compound of the formula

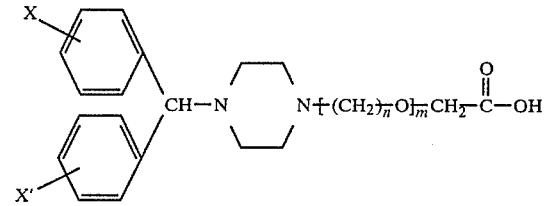

wherein
X and X' represents independently a hydrogen atom, a halogen atom, a straight or branched chain lower alkoxy radical or a trifluoromethyl radical,
m is 1 or 2, and
n is 1 or 2
or a non-toxic pharmaceutically acceptable salt thereof.

2. A compound or non-toxic pharmaceutically acceptable salt thereof according to claim 1 wherein n is 2.

3. A compound according to claim 1, said compound being 2-[2-[4-[(4-chlorophenyl)phenylmethyl]-1-piperazinyl]ethoxy]-acetic acid or a non-toxic pharmaceutically acceptable salt thereof.

4. A compound as claimed in claim 1, namely potassium 2-[2-[4-[(4-chlorophenyl)phenylmethyl]-1-piperazinyl]ethoxy]-acetate.

5. A compound as claimed in claim 1, namely 2-[2-[4-(diphenylmethyl)-1-piperazinyl]ethoxy]-acetic acid or its dihydrochloride.

6. A compound as claimed in claim 1, namely 2-[2-[4-[(4-fluorophenyl)phenylmethyl]-1-piperazinyl]ethoxy]-acetic acid or its hydrate.

7. The compound 2-[2-[4-[(4-chlorophenyl)phenylmethyl]-1-piperazinyl]ethoxy]-acetic acid.

8. The substantially pure crystalline compound according to claim 7 having a melting point of 110°–115° C.

9. A non-toxic pharmaceutically acceptable salt of 2-[2-[4-[(4-chlorophenyl)phenylmethyl]-1-piperazinyl]ethoxy]-acetic acid.

10. The dihydrochloride of 2-[2-[4-[(4-chlorophenyl)phenylmethyl]-1-piperazinyl]ethoxy]-acetic acid.

11. The substantially pure dihydrochloride of 2-[2-[4-[(4-chlorophenyl)phenylmethyl]-1-piperazinyl]ethoxy]-acetic acid having a melting point of about 225° C.

12. A pharmaceutical composition which comprises a pharmaceutically effective amount of a compound of the formula

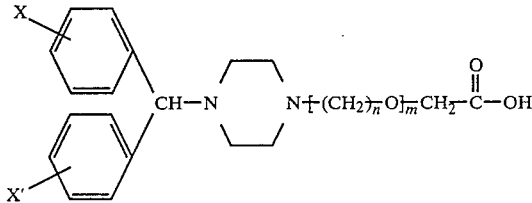

wherein
X and X' represent independently a hydrogen atom, a halogen atom, a straight or branched chain lower alkoxy radical or a trifluoromethyl radical,
m is 1 or 2, and
n is 1 or 2
or a non-toxic pharmaceutically acceptable salt thereof in association with a pharmaceutically acceptable carrier thereof.

13. An antihistaminic composition according to claim 12, said composition containing an antihistaminically effective amount of a compound of the formula

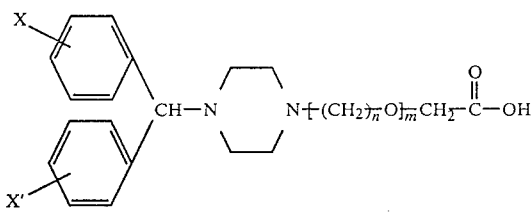

wherein
X and X' represent independently a hydrogen atom, a halogen atom, a straight or branched chain lower alkoxy radical or a trifluoromethyl radical,
m is 1 or 2, and
n is 1 or 2
or a non-toxic pharmaceutically acceptable salt thereof.

14. An antihistaminic composition according to claim 13, said composition containing an antihistaminically effective amount of 2-[2-[4-[(4-chlorophenyl)phenylmethyl]-1-piperazinyl]ethoxy]-acetic acid or a non-toxic pharmaceutically acceptable salt thereof.

15. A composition according to claim 13 containing an antihistaminically effective amount of a non-toxic pharmaceutically acceptable salt of 2-[2-[4-[(4-chlorophenyl)phenylmethyl]-1-piperazinyl]ethoxy]-acetic acid.

16. A composition according to claim 15 containing an antihistaminically effective amount of the dihydrochloride of 2-[2-[4-[(4-chlorophenyl)phenylmethyl]-1-piperazinyl]ethoxy]-acetic acid.

17. A composition according to claim 16 in dosage unit form containing from 0.5 to 250 mg of the said dihydrochloride.

18. A composition according to claim 17 in orally administrable dosage unit form.

19. An antiallergic composition comprising an antiallergically effective amount of a compound of the formula

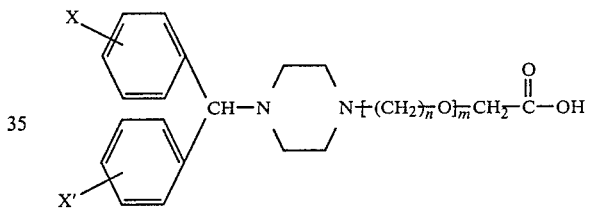

wherein
X and X' represent independently a hydrogen atom, a halogen atom, a straight or branched chain lower alkoxy radical or a trifluoromethyl radical,
m is 1 or 2, and
n is 1 or 2
or a non-toxic pharmaceutically acceptable salt thereof in association with a pharmaceutically acceptable carrier therefor.

20. A composition according to claim 19, said composition containing an antiallergically effective amount of 2-[2-[4-[(4-chlorophenyl)phenylmethyl]-1-piperazinyl]ethoxy]-acetic acid or a non-toxic pharmaceutically acceptable salt thereof.

21. A composition according to claim 20 containing a non-toxic pharmaceutically acceptable salt of 2-[2-[4-[(4-chlorophenyl)-phenylmethyl]-1-piperazinyl]ethoxy]-acetic acid.

22. A composition according to claim 21 containing the dihydrochloride of 2-[2-[4-[(4-chlorophenyl)phenylmethyl]-1-piperazinyl]ethoxy]-acetic acid.

23. A method for achieving an antiallergic, antihistaminic, bronchodilator or antispasmodic effect in a patient in need thereof which comprises administering to said patient an effective amount of a compound of the formula

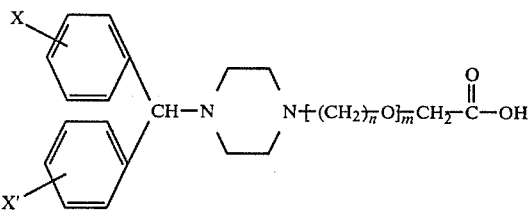

wherein
X and X' represent independently a hydrogen atom, a halogen atom, a straight or branched chain lower alkoxy radical or a trifluoromethyl radical,
m is 1 or 2, and
n is 1 or 2
or a non-toxic pharmaceutically acceptable salt thereof.

24. A method for achieving an antihistaminic effect in a patient in need thereof which comprises administering to said patient an antihistaminically effective amount of 2-[2-[4-[(4-chlorophenyl)phenylmethyl]-1-piperazinyl]ethoxy]-acetic acid or a non-toxic pharmaceutically acceptable salt thereof.

25. A method according to claim 24 wherein a non-toxic pharmaceutically acceptable salt of 2-[2-[4-[(4-chlorophenyl)phenylmethyl]-1-piperazinyl]ethoxy]-acetic acid is employed.

26. A method according to claim 25 wherein the dihydrochloride of 2-[2-[4-[(4-chlorophenyl)phenylmethyl]-1-piperazinly]ethoxy]-acetic acid is employed.

27. A method according to claim 26 wherein the administration is by the oral route.

28. A method for the treatment of allergic symptoms in a patient in need thereof which comprises administering to said patient an antiallergically effective amount of

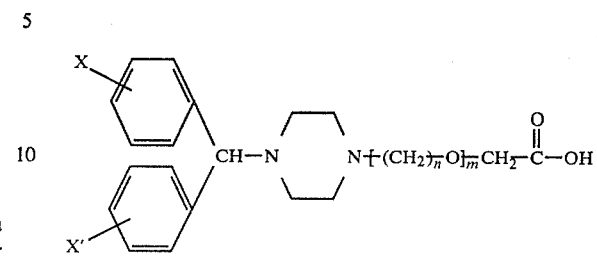

wherein
X and X' represent independently a hydrogen atom, a halogen atom, a straight or branched chain lower alkoxy radical or a trifluoromethyl radical,
m is 1 or 2, and
n is 1 or 2
or a non-toxic pharmaceutically acceptable salt thereof.

29. A method according to claim 28 wherein 2-[2-[4-[(4-chlorophenyl)phenylmethyl]-1-piperazinyl]ethoxy]-acetic acid or a non-toxic pharmaceutically acceptable salt thereof is employed.

30. A method according to claim 29 wherein a non-toxic pharmaceutically acceptable salt of 2-[2-[4-[(4-chlorophenyl)phenylmethyl]-1-piperazinyl]ethoxy]-acetic acid is employed.

31. A method according to claim 30 wherein the dihydrochloride of 2-[2-[4-[(4-chlorophenyl)phenylmethyl]-1-piperazinyl] ethoxy]-acetic acid is employed.

* * * * *

UNITED STATES PATENT AND TRADEMARK OFFICE

CERTIFICATE EXTENDING PATENT TERM
UNDER 35 U.S.C. § 156

PATENT NO.      :   4,525,358

ISSUED          :   June 25, 1985

INVENTOR(S)     :   Eugène Baltes et al.

PATENT OWNER    :   UCB Pharma, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 5 years from the original expiration date of the patent, June 25, 2002, with all rights pertaining thereto as provided by 35 U.S.C. § 156(b).

I have caused the seal of the Patent and Trademark Office to be affixed this 21st day of April 1997.

Bruce A. Lehman
Assistant Secretary of Commerce and
Commissioner of Patents and Trademarks